United States Patent [19]

Kawata

[11] Patent Number: 5,407,352

[45] Date of Patent: Apr. 18, 1995

[54] TRANSPARENT DENTAL TUBE UNIT

[75] Inventor: Sosaku Kawata, Kanuma, Japan

[73] Assignee: Nakanishi Dental Mfg. Co., Ltd., Japan

[21] Appl. No.: 131,494

[22] Filed: Oct. 4, 1993

[30] Foreign Application Priority Data

Oct. 8, 1992 [JP] Japan .................. 4-070264 U

[51] Int. Cl.⁶ .............................................. A61C 1/10
[52] U.S. Cl. ...................................... 433/84; 433/132
[58] Field of Search ............... 433/132, 84, 88, 91, 433/96

[56] References Cited

U.S. PATENT DOCUMENTS

| 3,077,333 | 2/1963 | Gotwald, Jr. et al. | 433/132 |
| 5,088,924 | 2/1992 | Woodward | 433/29 |
| 5,235,732 | 8/1993 | Bentley | 27/24.1 |

Primary Examiner—Cary E. O'Connor
Attorney, Agent, or Firm—Malcolm B. Wittenberg

[57] ABSTRACT

A transparent dental tube unit contains a transparent turbine gas supply passage for allowing a pressurized gas supplied from a pressurized fluid supply source to be passed to a dental handpiece for driving a turbine provided in the handpiece, a transparent liquid supply passage for allowing a pressurized liquid from the pressurized fluid source to be passed to the dental handpiece for dissipating the heat generated by friction, a transparent enclosure tube for enclosing the transparent turbine gas supply passage and the transparent liquid supply passage therein, and a fixing device for fixing the transparent turbine gas supply passage and the transparent liquid supply passage.

16 Claims, 3 Drawing Sheets

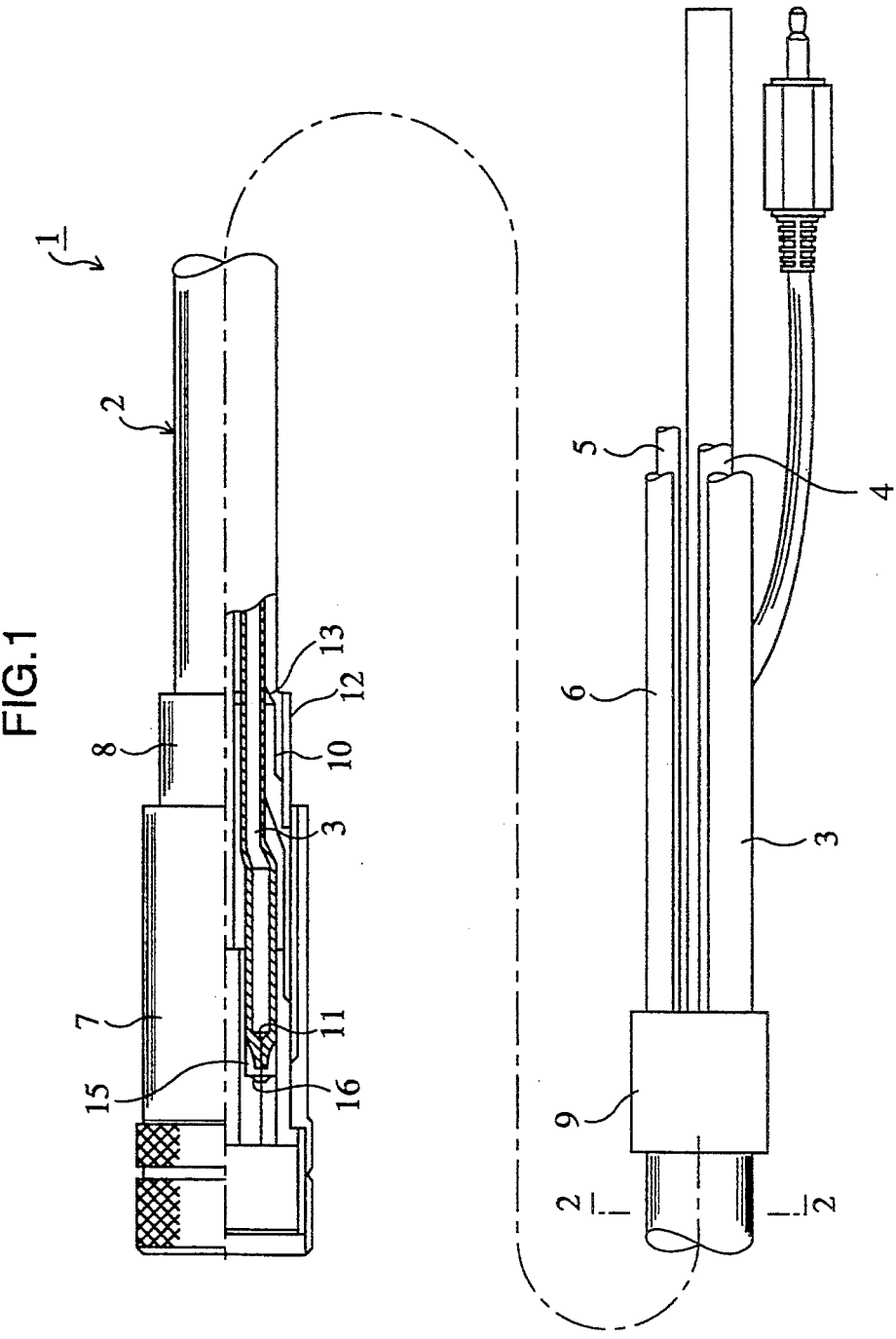

TRANSPARENT DENTAL TUBE UNIT

BACKGROUND OF THE INVENTION

This invention relates to a transparent dental tube unit and, more particularly, to a transparent dental tube for supplying a fluid under pressure, such as water or air, to the foremost part of a main body of a dental handpiece.

A dental tube unit employed for dental treatment is made up of a dental handpiece, a fluid supply source for supplying the fluid, such as water or air, under pressure, and a tube unit used as passages for air or water from the supply source to the handpiece. The tube unit includes an air supply tube, an air discharge tube, a water supply tube for supplying water to the foremost part of the handpiece, and an outer enclosure tube enclosing therein the air supply tube, the air discharge tube and the water supply tube. The air supplied under pressure from the fluid supply source through the air supply tube to the main body of the handpiece is used for running a turbine mechanism disposed at a head part of the handpiece in rotation so as to be then discharged via the air discharge tube. On the other hand, the water supply tube is used for supplying water from the supply source to the dental handpiece or for cooling the teeth which have become hot under the heat of friction generated during the dental treatment. It is noted that there are occasions wherein the air is discharged without passing through the air discharge tube.

However, it is known that when the operation of the turbine of the dental handpiece is halted, the tooth debris or saliva or the like impurities from the oral cavity of the patient tend to be sucked into the inside of the handpiece and into the inside of the tube. Consequently, the inside of the tube is contaminated and there arises the risk of transmission of an infectious disease such as B-hepatitis from a host patient to other patients. For this reason, it is necessary that not only the dental handpiece but also the above-mentioned tubes be disinfected by an autoclave or exchanged with new ones. Besides, it is necessary to check the status of contamination within the tube from time to time. On the other hand, the status of contamination within the inside of the tube cannot be checked with ease.

There has not hitherto been made a proposal for providing a device for preventing the contamination of the dental tube unit.

SUMMARY OF THE INVENTION

It is an object of the present invention to provide a transparent dental tube unit in which the status of suction of impurities into the tubes and further the status of contamination of the handpiece itself may be noticed at a glance.

It is another object of the present invention to provide a transparent dental tube unit in which the status of contamination of the tube may be noticed at a glance and accordingly the inside of the tube may be disinfected, rinsed or exchanged and further the handpiece, and the tube unit may be rinsed or processed otherwise as the occasion may demand.

It is a further object of the present invention to provide a transparent dental tube unit having a device for inhibiting the contamination.

The above and other Objects of the invention will become apparent from the following description.

According to the present invention, there is provided a transparent dental tube unit comprising a transparent turbine gas supply passage for allowing a pressurized gas supplied from a pressurized fluid supply source to be passed to a dental handpiece for driving a turbine provided in the handpiece, a transparent liquid supply passage for allowing a pressurized liquid from the pressurized fluid source to be passed to the dental handpiece for dissipating the heat generated by friction, a transparent enclosure tube for enclosing the transparent turbine gas supply passage and the transparent liquid supply passage therein, and fixing means for fixing the transparent turbine gas supply passage and the transparent liquid supply passage.

BRIEF DESCRIPTION OF THE DRAWINGS

FIG. 1 is a schematic overall side view showing transparent tubes for a dental unit according to the present invention, with the tube being shown partially in section.

PREFERRED EMBODIMENTS OF THE INVENTION

Figure 3A:
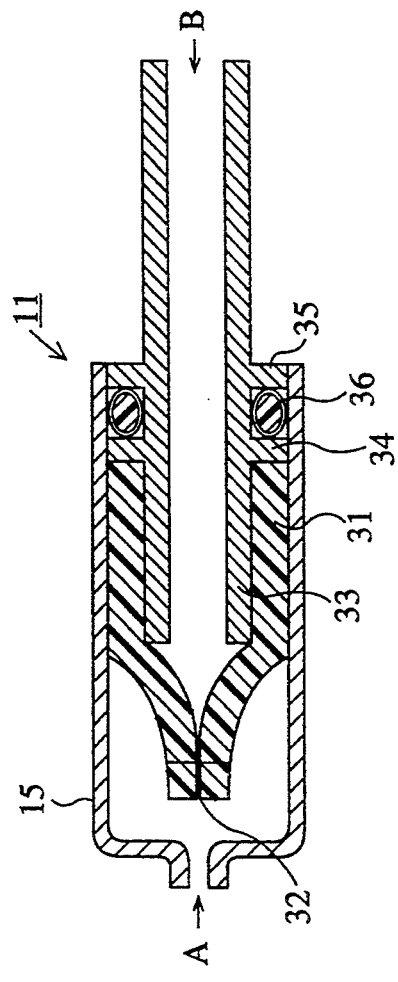
FIG. 3A is a cross-sectional view showing a check valve of FIG. 1 in detail.

FIG. 1 schematically illustrates, in an overall view, a transparent tube unit 1 according to the present invention, with a part of the tube being shown in cross-section. The transparent tube unit 1 is made up of an air supply tube 3, an air discharge tube 4, shown in FIG. 2, a water supply tube 5, a chip air tube 6, an outer enclosure tube 2 enclosing the tubes 3 to 6 and lead wires 14 shown in FIG. 2, tube fixing metal fixtures 8, 9 for securing the tubes 3 to 6 within the outer enclosure tube 2 against distortion at the front and rear ends of the outer enclosure tube 2, and a connector ring 7 connected to the tube fixing metal fixture 8 and to the main body of the dental handpiece, as explained in more detail hereinbelow. The outer enclosure tube 2 is fitted into a space between an outer tube 12 of the metal fixtures 8 and an inner tube 13 having a volute joint 10 on the outer periphery thereof, while the air supply tube 3, the air discharge tube 4, the water supply tube 5 and the chip air tube 6 are supported within the outer enclosure tube 2 at a constant distance from one another.

FIG. 1 shows a transparent dental tube unit according to the present invention, in which a check valve 11 is enclosed within the air supply tube 3 at the foremost part thereof. The connector ring and the tube fixing metal fixture 8 are detachably connected to each other by a protrusion in the form of an attachment plug 15 fixedly provided on the side of the tube fixing metal fixture 8 and a receptacle-shaped recess 16 provided on the side of the connector ring for being mated with the protrusion 15. The check valve 11 is explained subsequently in more detail.

Figure 2:
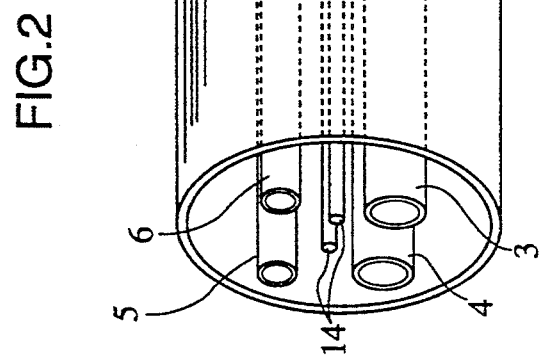
FIG. 2 is a perspective view cut along line 2—2 in FIG. 1, with the inside of the tubes being partially seen from outside.

FIG. 2 shows the transparent dental tube unit 1 in a perspective view looking in the direction of line 2—2 in FIG. 1. The main components of the tube unit 1 include the air supply tube 3, the air discharge tube 4, the air supply tube 5, the chip air tube 6 and the outer enclosure tube 2 enclosing these tubes 3 to 6. Of these, the air supply tube 3 is a passage for air supplied from a pressurized gas supply source, not shown, for running the turbine of the dental handpiece in rotation, while the air discharge tube 4 is a passage for the air which has been used for running the turbine in rotation and which is to be discharged to outside after passage through the air discharge tube. The water supply tube 5 guides water from its supply source, not shown, to the handpiece so that the water may be used for dissipating the heat generated under friction between the teeth and the dental tool. The chip air tube 6 is a passage for intermittently supplying the air for scattering the tooth debris.

Meanwhile, the tubes enclosed in the outer enclosure tube 2 are not limited to the air supply tube 3, the air discharge tube 4, the water supply tube 5 or the chip air tube 6 used in the present embodiment, since a variety of dental handpieces are presently available and the present invention may be adapted for use with these existing handpieces.

These tubes are formed of a material having high safety and superior transparency and resistance against chemicals. Examples of the material include fluororesin elastomers composed of a fluororesin, e.g. ethylene tetrafluoroethylene (ETFE) and a fluororubber, e.g. fluorinated vinylidene fluoride-hexafluoropropylene-tetraflugroethylene.

Figure 3B:
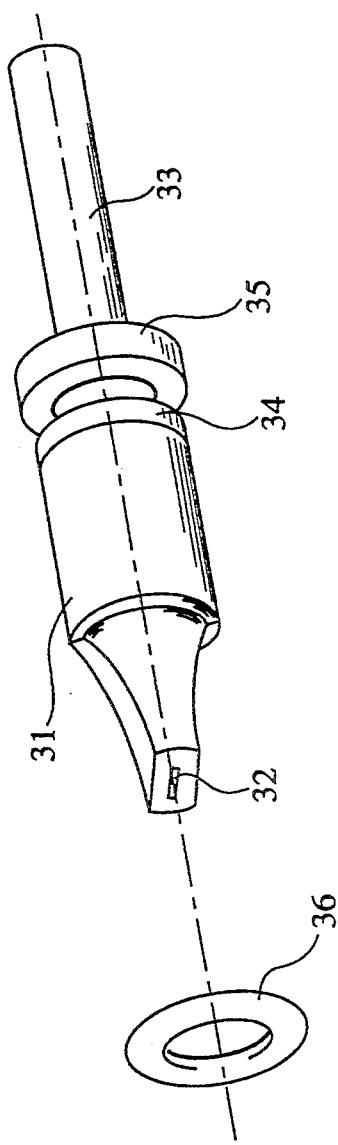
FIG. 3B is an exploded perspective view showing the check valve shown in FIG. 3A.

Referring to FIGS. 3A and 3B, the check valve 11 shown in FIG. 1 is explained in detail. Within the attachment plug type formed of an elastic material, such as rubber. An opening 32 is protrusion 15 is mounted a valve member 31 of a duck bill type formed of an elastic material, such as rubber. An opening 32 is formed at the foremost part of the valve member 31. When air flows in the direction shown by an arrow A, the opening 32 remains closed under elasticity of the valve member 31 as shown. When air flows in the direction shown by an arrow B, the opening 32 is opened against the elasticity of the valve member 31 to permit air to pass therethrough in such direction. The valve member 31 is secured in position by being fitted over a conduit 33 within the protrusion 15. The conduit 33 is formed with flanges 34, 35 between which a rubber ring 36 is fitted to prevent air leakage. By the provision of the check valve 11, the risk of possible contamination of the air supply tube 3 may be completely eliminated even if impurities are sucked at the foremost part of the handpiece. A check valve similar to the check valve 11 provided in the air supply tube 3 may also be provided in the air discharge tube 4, the water supply tube 5 or the chip air tube 6. When the check valve 11 is provided in the air discharge tube 4, the check valve 11 is mounted in the opposite direction to that of the check valve 11 provided in the air supply tube 4 so that air may normally be discharged from the handpiece towards the transparent tube unit 1. If the check valves 11 are provided in both the air supply tube 3 and the air discharge tube 4, when impurities are sucked from the foremost part of the handpiece, the air flow is reversed so that both of the check valves are actuated simultaneously to assure complete prevention of suction of impurities.

Figure 4A:
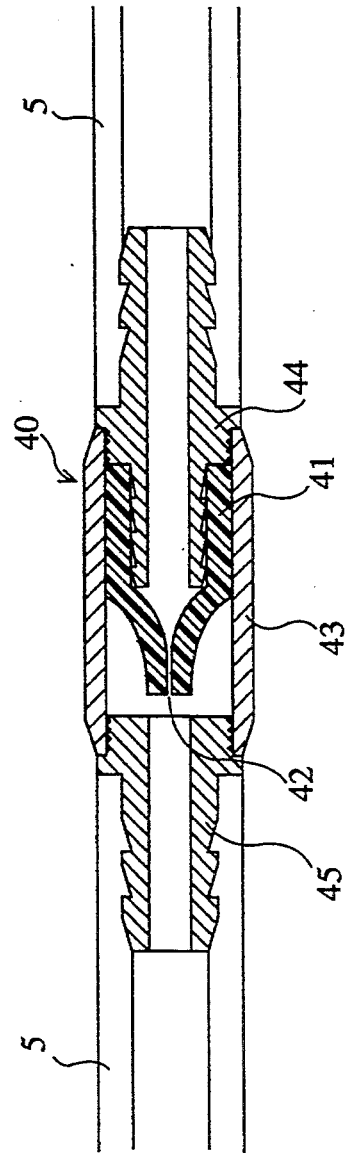
FIG. 4A is a cross-sectional view showing another check valve mounted halfway in a transparent water supply tube in detail.
Figure 4B:
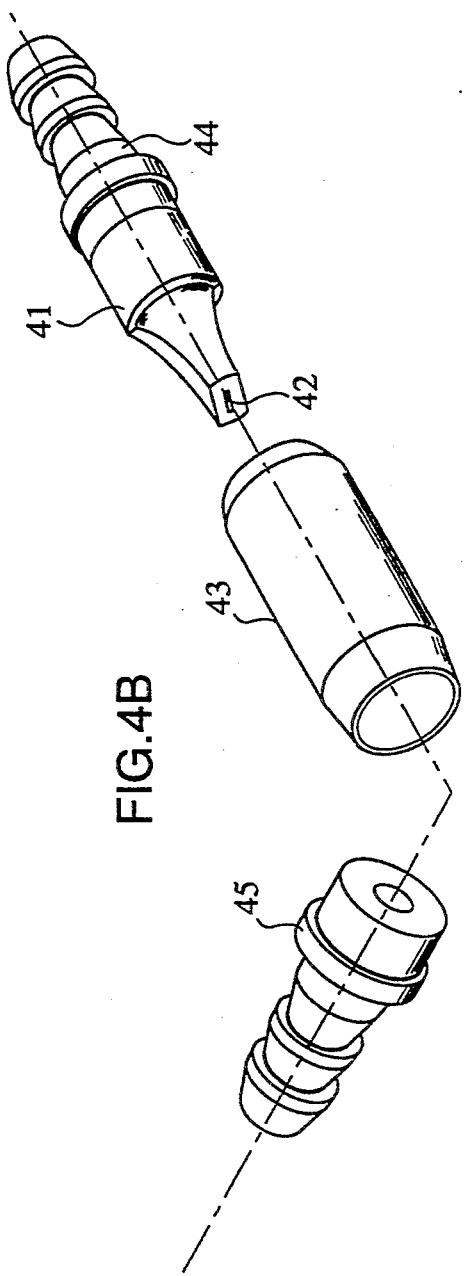
FIG. 4B is an exploded perspective view showing the check valve shown in FIG. 4A.

FIGS. 4A and 4B illustrate a modified embodiment in which a valve member 41 similar to the valve member 31 shown in FIGS. 3A and 3B is provided halfway in the transparent water supply tube 5. An opening 42 is formed in the foremost part of the valve member 41 and functions in the same way as the opening 32 described above. The valve member 41 is secured in position between a tubular member 43 and a rear fixing tube 44 to the rear part of which the water supply tube 5 is secured. A front fixing tube 48 is threadedly attached to the tubular member 43 and the water supply tube 5 is fixedly attached to the foremost part of the front fixing tube 45. If such check valve is provided in each of the transparent tubes 3 to 6, the tubular member 43 may also be formed of a transparent material, in which case operational troubles of the valve member 41 may be noticed at a glance, so that repair or exchange may be undertaken immediately.

If the check valves 11, 40 are provided in one and the same tube, such as the air supply tube 3, contamination due to the flow reversal may be prevented more positively.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A transparent dental tube unit comprising:
   a transparent turbine gas supply passage for allowing a pressurized gas supplied form a pressurized fluid supply source to be passed to a dental handpiece for driving a turbine provided in said handpiece;
   a transparent liquid supply passage for allowing a pressurized liquid from said pressurized fluid source to be passed to said dental handpiece for dissipating heat generated by friction;
   a transparent enclosure tube for enclosing said transparent turbine gas supply passage and said transparent liquid supply passage therein; and
   fixing means for fixing said transparent turbine gas supply passage and said transparent liquid supply passage,
   characterized in that said tube unit further comprises at least one check valve in said transparent turbine gas supply passage for preventing flow reversal.

2. The tube unit as claimed in claim 1 wherein said check valve is connected to a conduit provided at a foremost part of said transparent turbine gas supply passage.

3. The tube unit as claimed in claim 1 wherein said check valve is provided halfway in said transparent turbine gas supply passage.

4. The tube unit as claimed in claim 3 wherein said check valve comprises a valve body for allowing fluid to pass therethrough and a transparent enclosure for fixing the valve body therein.

5. A transparent dental tube unit comprising:
   a transparent turbine gas supply passage for allowing a pressurized gas supplied from a pressurized fluid supply source to be passed to a dental handpiece for driving a turbine provided in said handpiece;
   a transparent liquid supply passage for allowing a pressurized liquid from said pressurized fluid source to be passed to said dental handpiece for dissipating heat generated by friction;

a transparent enclosure tube for enclosing said transparent turbine gas supply passage and said transparent liquid supply passage therein; and fixing means for fixing said transparent turbine gas supply passage and said transparent liquid supply passage, characterized in that said tube unit further comprises at least one check valve in said transparent liquid supply passage for preventing flow reversal.

6. The tube unit as claimed in claim 5 wherein said check valve is connected to a conduit provided at a foremost part of said transparent liquid supply passage.

7. The tube unit as claimed in claim 5 wherein said check valve is provided halfway in said transparent liquid supply passage.

8. The tube unit as claimed in claim 7 wherein said check valve comprises a valve body for allowing fluid to pass therethrough and a transparent enclosure for fixing the valve body therein.

9. A transparent dental tube unit comprising:
a transparent turbine gas supply passage for allowing a pressurized gas supplied from a pressurized fluid supply source to be passed to a dental handpiece for driving a turbine provided in said handpiece;

a transparent liquid supply passage for allowing a pressurized liquid from said pressurized fluid source to be passed to said dental handpiece for dissipating heat generated by friction;

a transparent enclosure tube for enclosing said transparent turbine gas supply passage and said transparent liquid supply passage therein;

fixing means for fixing said transparent turbine gas supply passage and said transparent liquid supply passage; and a transparent turbine gas discharge passage for discharging the pressurized gas from said handpiece after the gas is allowed to be passed through said handpiece;

characterized in that said tube unit further comprises at least one check valve in said transparent turbine gas discharge passage for preventing flow reversal.

10. The tube unit as claimed in claim 9 wherein said check valve is provided halfway in said transparent turbine gas discharge passage.

11. The tube unit as claimed in claim 10 wherein said check valve comprises a valve body for allowing fluid to pass therethrough and a transparent enclosure for fixing the valve body therein.

12. A transparent dental tube unit comprising:
a transparent turbine gas supply passage for allowing a pressurized gas supplied from a pressurized fluid supply source to be passed to a dental handpiece for driving a turbine provided in said handpiece;

a transparent liquid supply passage for allowing a pressurized liquid from said pressurized fluid source to be passed to said dental handpiece for dissipating heat generated by friction;

a transparent enclosure tube for enclosing said transparent turbine gas supply passage and said transparent liquid supply passage therein;

fixing means for fixing said transparent turbine gas supply passage and said transparent liquid supply passage; and a transparent chip gas supply passage for allowing a pressurized gas supplied from said pressurized fluid supply source for scattering tooth chip to be passed to said dental handpiece;

characterized in that said tube unit further comprises at least one check valve in said transparent chip gas supply passage for preventing flow reversal.

13. The tube unit as claimed in claim 12 wherein said check valve is connected to a conduit provided at a foremost part of said transparent chip gas supply passage.

14. The tube unit as claimed in claim 12 wherein said check valve is provided halfway in said transparent chip gas supply passage.

15. The tube unit as claimed in claim 14 wherein said check valve comprises a valve body for allowing fluid to pass therethrough and a transparent enclosure for fixing the valve body therein.

16. A transparent dental tube unit comprising:
a transparent turbine gas supply passage for allowing a pressurized gas supplied from a pressurized fluid supply source to be passed to a dental handpiece for driving a turbine provided in said handpiece;

a transparent liquid supply passage for allowing a pressurized liquid from said pressurized fluid source to be passed to said dental handpiece for dissipating heat generated by friction;

a transparent enclosure tube for enclosing said transparent turbine gas supply passage and said transparent liquid supply passage therein; and fixing means for fixing said transparent turbine gas supply passage and said transparent liquid supply passage;

characterized in that said tube unit further comprises:
a transparent turbine gas discharge passage for discharging the pressurized gas from said handpiece after the gas is allowed to be passed through said handpiece, and at least one check valve in each of said transparent turbine gas supply passage and said transparent turbine gas discharge passage for preventing flow reversal.

* * * * *

UNITED STATES PATENT AND TRADEMARK OFFICE
CERTIFICATE OF CORRECTION

PATENT NO. : 5,407,352

DATED : April 18, 1995

INVENTOR(S) : Kawata

It is certified that error appears in the above-identified patent and that said Letters Patent is hereby corrected as shown below:

Column 4, line 32, delete "form" and insert therefore --from--.

Signed and Sealed this

Seventeenth Day of October, 1995

*Attest:*

BRUCE LEHMAN

*Attesting Officer*     *Commissioner of Patents and Trademarks*